United States Patent
Kasai et al.

(10) Patent No.: US 8,890,068 B2
(45) Date of Patent: Nov. 18, 2014

(54) CHARGED PARTICLE RAY APPARATUS AND PATTERN MEASUREMENT METHOD

(75) Inventors: Yuji Kasai, Tokyo (JP); Makoto Suzuki, Tokyo (JP); Hiroshi Makino, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/002,275

(22) PCT Filed: Jan. 27, 2012

(86) PCT No.: PCT/JP2012/051812
§ 371 (c)(1),
(2), (4) Date: Aug. 29, 2013

(87) PCT Pub. No.: WO2012/127901
PCT Pub. Date: Sep. 27, 2012

(65) Prior Publication Data
US 2014/0001360 A1    Jan. 2, 2014

(30) Foreign Application Priority Data

Mar. 24, 2011    (JP) ................................. 2011-066724

(51) Int. Cl.
| | | |
|---|---|---|
| H01J 37/05 | (2006.01) | |
| H01J 37/244 | (2006.01) | |
| H01J 37/28 | (2006.01) | |
| G01N 23/225 | (2006.01) | |
| G06T 1/00 | (2006.01) | |

(52) U.S. Cl.
CPC ....... *H01J 37/05* (2013.01); *H01J 2237/24485* (2013.01); *H01J 37/244* (2013.01); *H01J 2237/2449* (2013.01); *H01J 2237/24495* (2013.01); *G06T 1/00* (2013.01); *H01J 37/28* (2013.01); *H01J 2237/24475* (2013.01)
USPC ............................. 250/310; 250/307; 250/305

(58) Field of Classification Search
CPC . G01N 23/225; G01N 23/2251; H01J 37/244; H01J 37/05; H01J 37/26; H01J 37/261; H01J 37/263; H01J 37/265; H01J 37/28; H01J 37/29; H01J 37/292; H01J 37/252; H01J 37/256; H01J 37/268; H01J 2237/05; H01J 2237/053; H01J 2237/057; H01J 2237/24495; H01J 2237/2522; H01J 2237/2561; H01J 2237/2804; H01J 2237/2806; H01J 2237/2817
See application file for complete search history.

(56) References Cited

U.S. PATENT DOCUMENTS

| | | | |
|---|---|---|---|
| 5,644,132 A | 7/1997 | Litman et al. | |
| 6,426,501 B1 | 7/2002 | Nakagawa | |

(Continued)

FOREIGN PATENT DOCUMENTS

| | | | |
|---|---|---|---|
| JP | 8-273569 A | 10/1996 | |
| JP | 2000-48752 A | 2/2000 | |

(Continued)

OTHER PUBLICATIONS

Japanese-language Written Opinion dated Mar. 27, 2012 (Four (4) pages).
International Search Report dated Mar. 27, 2012 with English translation (Five (5) pages).

*Primary Examiner* — Jack Berman
(74) *Attorney, Agent, or Firm* — Crowell & Moring LLP

(57) ABSTRACT

Provided is a technique to automatize a synthesis function of signal charged particles having different energies. A charged particle beam apparatus includes: a charged particle source configured to irradiate a sample with a primary charged particle ray; a first detector configured to detect a first signal electron having first energy from signal charged particles generated from the sample; a second detector configured to detect a second signal electron having second energy from signal charged particles generated from the sample; a first operation part configured to change a synthesis ratio of a signal intensity of the first signal electron and a signal intensity of the second signal electron and to generate a detected image corresponding to each synthesis ratio; a second operation part configured to calculate a ratio of signal intensities corresponding to predetermined two areas of the detected image generated for each synthesis ratio; and a third operation part configured to determine a mixture ratio to be used for acquisition of the detected image on a basis of a change of the ratio of signal intensities.

14 Claims, 16 Drawing Sheets

(56) References Cited

U.S. PATENT DOCUMENTS

| | | |
|---|---|---|
| 6,667,476 B2 * | 12/2003 | Todokoro et al. ............. 250/397 |
| 8,076,642 B2 * | 12/2011 | Kazumori ..................... 250/310 |
| 2004/0051041 A1 | 3/2004 | Todokoro et al. |
| 2011/0155905 A1 | 6/2011 | Hatakeyama et al. |

FOREIGN PATENT DOCUMENTS

| | | |
|---|---|---|
| JP | 2001-357808 A | 12/2001 |
| JP | 2004-14229 A | 1/2004 |
| JP | 4069624 B2 | 1/2008 |
| WO | WO 2009/125603 A1 | 10/2009 |

* cited by examiner (a)

(b)                      (c)

Cross section 1                 Cross section 2

(a)

Step 401 executed (b)

Step 404 executed (c)

Step 406 executed (a)

(b)

(c)

CHARGED PARTICLE RAY APPARATUS AND PATTERN MEASUREMENT METHOD

TECHNICAL FIELD

The present invention relates to a charged particle ray (beam) apparatus that detects signal electrons generated from a sample irradiated with a charged particle beam and generates an image thereof, and a method for measuring a pattern of a surface of the sample based on the image.

BACKGROUND ART

Higher integration of semiconductor devices have increased the importance to control pattern on the outermost face as well as to perform alignment control (shape control) of an upper-layer pattern and a lower-layer pattern and dimension control of a hole opening. A scanning electron microscope (hereinafter called a SEM) has been used typically for the shape control and the dimension control of such a multi-layered device (three-dimensional device).

Patent Literature 1 discloses a SEM provided with an energy filter capable of selecting signal electrons detected according to their energies. This type of SEM adjusts a threshold voltage of the energy filter, whereby a contrast image corresponding to a difference in surface potential of the device can be obtained.

Patent Literature 2 discloses a SEM including a detector for back scattered electrons and a detector for secondary electrons mounted thereon.

CITATION LIST

Patent Literature

Patent Literature 1: Japanese Patent No. 4069624
Patent Literature 2: JP Patent Publication No. 08-273569 (1996)

SUMMARY OF INVENTION

Technical Problem

A method for automatically setting threshold voltage of the energy filter for each observed device has not been known. This makes it difficult to mount an energy filter on a shape control/dimension control apparatus of a semiconductor device that requires automation and speeding up.

An image of back scattered electrons has a low contrast. This means the difficulty in measuring a pattern thereof simply based on the image of back scattered electrons. Then, it is reasonable to synthesize the image of back scattered electrons with the image of secondary electrons for shape control and dimension control.

Patent Literature 2, however, does not disclose a method of determining an optimum ratio for synthesis of the image of back scattered electrons and the image of secondary electrons. This makes it difficult to mount a synthesis function of the image of back scattered electrons and the image of secondary electrons to a shape control/dimension control device of a semiconductor device that requires automation and speeding up.

Solution to Problem

To solve the aforementioned problems, the present invention proposes a charged particle beam apparatus including: a charged particle source configured to irradiate a sample with a primary charged particle beam; a first detector configured to detect a first signal electron having first energy from signal charged particles generated from the sample; a second detector configured to detect a second signal electron having second energy from signal charged particles generated from the sample; a first operation part configured to change a synthesis ratio of a signal intensity of the first signal electron and a signal intensity of the second signal electron and to generate a detected image corresponding to each synthesis ratio; a second operation part configured to calculate a ratio of signal intensities corresponding to predetermined two areas of the detected image generated for each synthesis ratio; and a third operation part configured to determine a mixture ratio to be used for acquisition of the detected image on a basis of a change of the ratio of signal intensities.

To solve the aforementioned problems, the present invention proposes another charged particle ray (beam) apparatus including: a charged particle source configured to irradiate a sample with a primary charged particle beam; an energy filter configured to separate signal charged particles according to magnitude of energy; a detector configured to detect signal charged particles that have passed through the energy filter; a first operation part configured to change filter voltage to be applied to the energy filter and to generate a detected image corresponding to each filter voltage; a second operation part configured to calculate a ratio of signal intensities corresponding to predetermined two areas of the detected image generated for each filter voltage; and a third operation part configured to determine filter voltage to be used for acquisition of the detected image on a basis of a change of the ratio of signal intensities.

Advantageous Effects of Invention

According to the present invention, acquisition conditions required for automation of shape control and dimension control of a three-dimensional device can be set automatically. Problems, configurations, and advantageous effects other than those explained above will be made apparent from the following explanations of embodiments.

BRIEF DESCRIPTION OF DRAWINGS

FIG. 10-1 shows a relationship between energy distribution of signal electrons and signal intensity.
FIG. 10-2 explains how to determine optimum filter voltage when gray level ratio changes in pattern 1.
FIG. 10-3 explains how to determine optimum filter voltage when gray level ratio changes in pattern 2.

FIG. 10-4 explains how to determine an optimum synthesis ratio when gradation ratio changes in pattern 1.

FIG. 10-5 explains how to determine an optimum synthesis ratio when gradation ratio changes in pattern 2.

DESCRIPTION OF EMBODIMENTS

The following describes embodiments of the present invention, with reference to the drawings. The present invention is not limited to the following embodiments, and can be modified variously within the scope of its technical idea. The following description exemplifies a scanning electron microscope as one of charged particle ray (beam) apparatuses, and the present invention is applicable to a focused ion beam (FIB) microscope as well.

Exemplary Configuration 1

Overall Configuration

Figure 1:
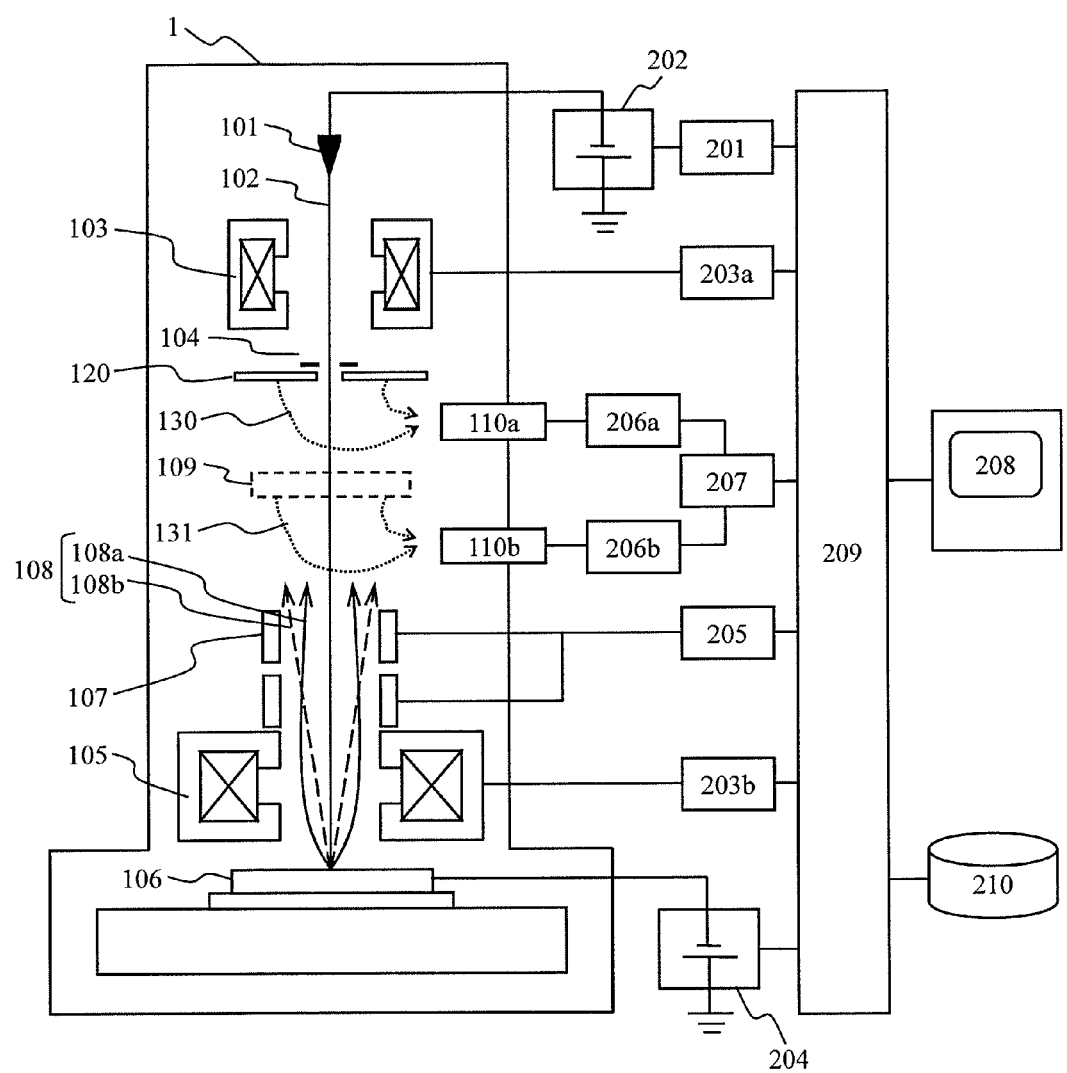
FIG. 1 shows a first exemplary configuration of a scanning electron microscope.

FIG. 1 shows a first exemplary configuration of a scanning electron microscope. The following describes an electron beam inspection apparatus that is used for observation of a circuit pattern or a resist pattern formed on a semiconductor wafer, their dimension measurement, shape measurement, inspections and defects reviews.

An electron microscope lens barrel 1 includes an electron emitting source 101 attached thereto. The electron emitting source 101 emits a primary electron beam 102 under the control of an electron source controller 201. The primary electron beam 102 is accelerated by electron source acceleration voltage 202 connected to the electron emitting source 101. Then, the primary electron beam 102 is optimized for its diameter by one or more focusing lenses 103 and a current limiting aperture 104. The focusing lenses 103 are controlled by a lens controller 203a. Then, the primary electron beam 102 is focused on the surface of a sample 106 via an objective lens 105. The objective lens 105 is controlled by a lens controller 203b.

Negative voltage (retarding voltage) 204 is applied to the sample 106. The application of the negative voltage (retarding voltage) 204 generates retarding field between the sample 106 and the objective lens 105. The retarding field decelerates the primary electron beam 102 immediately before the sample, and then the primary electron beam 102 arrives at the surface of the sample 106. Herein, incident voltage is given by the value of electron source accelerating voltage−retarding voltage.

The primary electron beam 102 is deflected by a deflector 107, thus scanning on the surface of the sample 106. At this time, signal electrons 108 are generated from the scanning position of the primary electron beam 102. Herein, the deflector 107 is controlled by a deflection controller 205.

The signal electrons 108 referred to in the present configuration include true secondary electrons (TSE) 108a having kinetic energy less than 50 eV and backscattered electrons (BSE) 108b having kinetic energy more than 50 eV.

The signal electrons 108 generated from the sample 106 are accelerated by the retarding voltage 204 and are incident on an energy filter 109. The signal electrons 108 that have passed through the energy filter 109 collide with a converting electrode 120, and so generate second secondary electrons 130. The second secondary electrons 130 are detected by a detector 110a. Secondary electrons 131 reflected from the energy filter 109 are detected by a detector 110b. Positive voltage is applied to the detector 110a and the detector 110b, and electric field generated by such voltage attracts the secondary electrons 130 and 131.

Signals detected at the detector 110a and the detector 110b are amplified by amplifiers 206a and 206b, respectively, and are input to a synthesis operation part 207. An image subjected to synthesis operation by the synthesis operation part 207 is displayed on a display 208.

The controllers 201, 203a, 203b and 205 are controlled by a central controller 209 in an integrated way. Control values and adjustment values are stored in a storage device 210.

Figure 2:
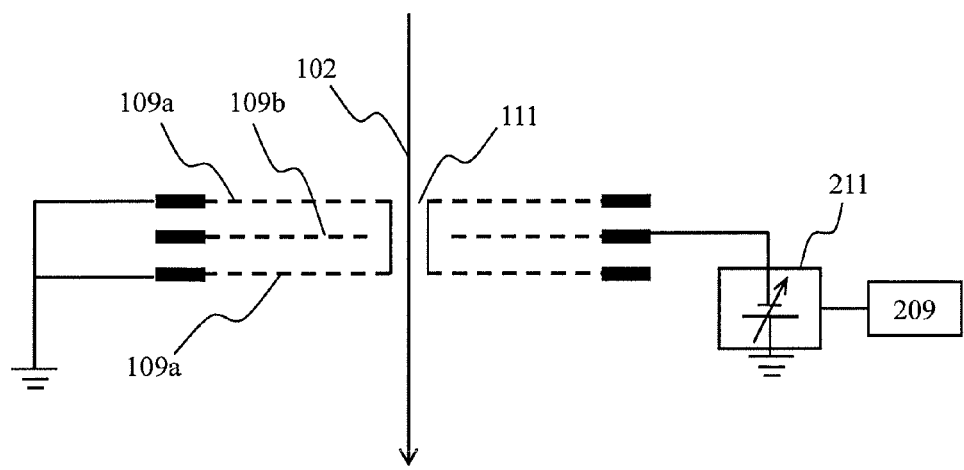
FIG. 2 shows an exemplary configuration of an energy filter.

FIG. 2 shows a basic configuration of the energy filter 109. The energy filter 109 includes two shield meshes 109a and one filter mesh 109b. These three meshes are provided with openings 111 to let the primary electron beam 102 pass therethrough.

To the filter mesh 109b, a filter power source 211 is connected to apply filter voltage. Similarly to other controllers, the filter power source 211 is controlled by the central controller 209. FIG. 2 shows one filter mesh 109b, but this may be a plurality of filter meshes. Such a plurality of filter meshes 109b may be independently connected to the filter power source 211.

Energy Distribution of Signal Electrons

Figure 3:
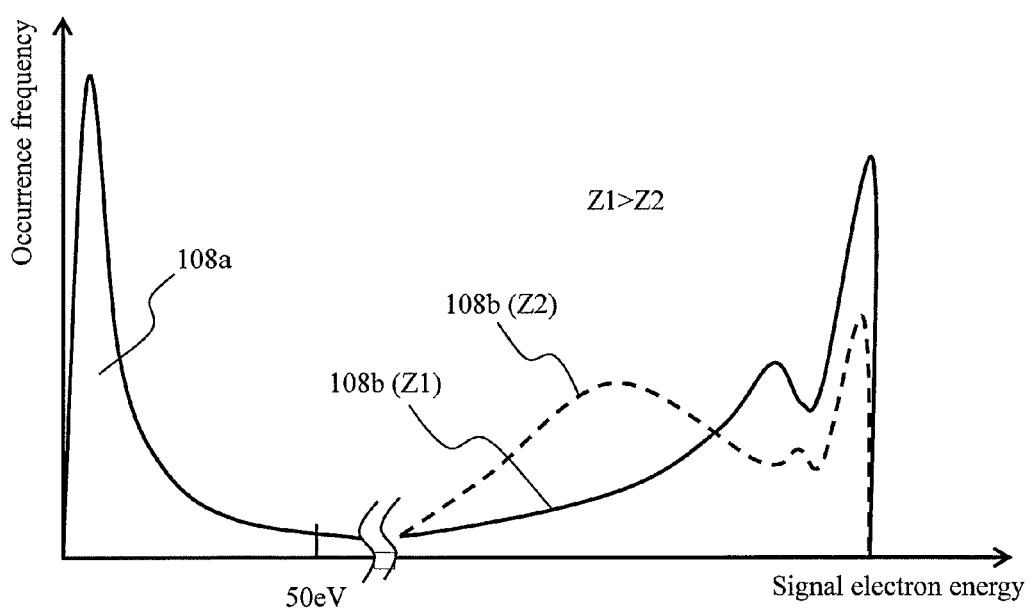
FIG. 3 shows energy distribution of signal electrons.

FIG. 3 schematically shows energy distribution of signal electrons. The horizontal axis represents energy of the signal electrons and the vertical axis represents occurrence frequency. As described above, the signal electrons include two types of electrons that are different in emission direction and energy. That is, they include true secondary electrons 108a and backscattered electrons 108b.

In FIG. 3, the energy distribution of the true secondary electrons 108a has a peak around from a few eV to 10 eV. On the other hand, the energy distribution of the backscattered electrons 108b strongly depends on the average atomic number of the sample 106. For instance, when the sample 106 has a large average atomic number (Z1), the distribution will be elastically scattered, having a peak at the energy substantially equal to the incident energy of the primary electron beam 102. When the sample 106 has a small average atomic number (Z2), the distribution has a peak at the energy about half of the incident energy of the primary electron beam 102. In FIG. 3, the waveform of the backscattered electrons 108b having smaller energy is represented by the broken line.

As shown in FIG. 3, the energy distribution of signal electrons actually generated during observation (measurement) varies with materials making up the sample 106. Therefore the synthesis ratio of two detected signals output from the two detectors 110a and 110b cannot be decided beforehand.

The following embodiments describe the processing functions of the synthesis operation part 207 and the central controller 209 to automatically adjust a synthesis ratio of these two detected signals and automatically implement shape control and dimension control of a three-dimensional device.

Embodiment 1

Figure 4:
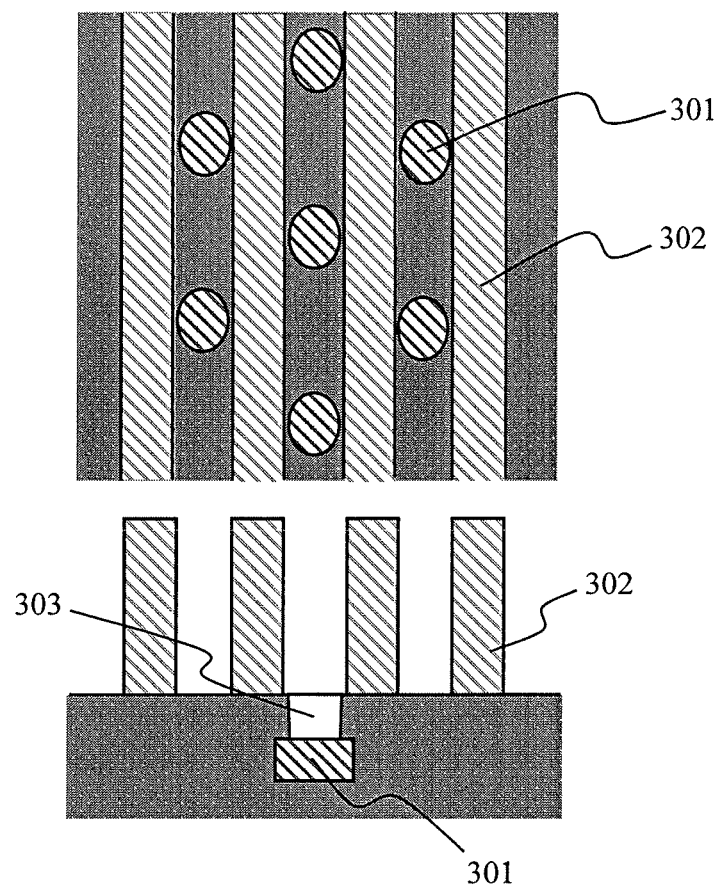
FIG. 4 shows an exemplary structure of a pattern that is a measurement target in Embodiment 1.

FIG. 4 shows an exemplary surface pattern of a three-dimensional device that is assumed as a measurement target. The upper part of the drawing is a plan view of the three-dimensional device, and the lower part is a cross-sectional view of the three-dimensional device. This three-dimensional device has a lowermost layer in which metal 301 is embedded, and a wiring pattern 302 including a plurality of parallel lines is formed at an upper layer. At a gap between the parallel lines of the wiring pattern, an opening 303 is formed at a base layer for continuity with the metal 301 at the lower layer.

For measurement of the dimensions of the opening 303 formed in this three-dimensional device, a bottom part of the gap and a metal part of the lower layer have to be made clear in the synthesis image.

Figure 5:
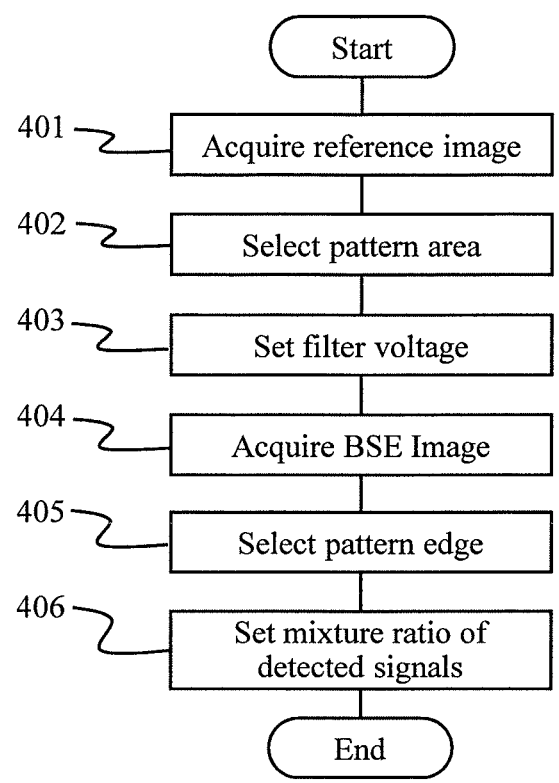
FIG. 5 is a flowchart to determine setting conditions of a detection system.
Figure 6:
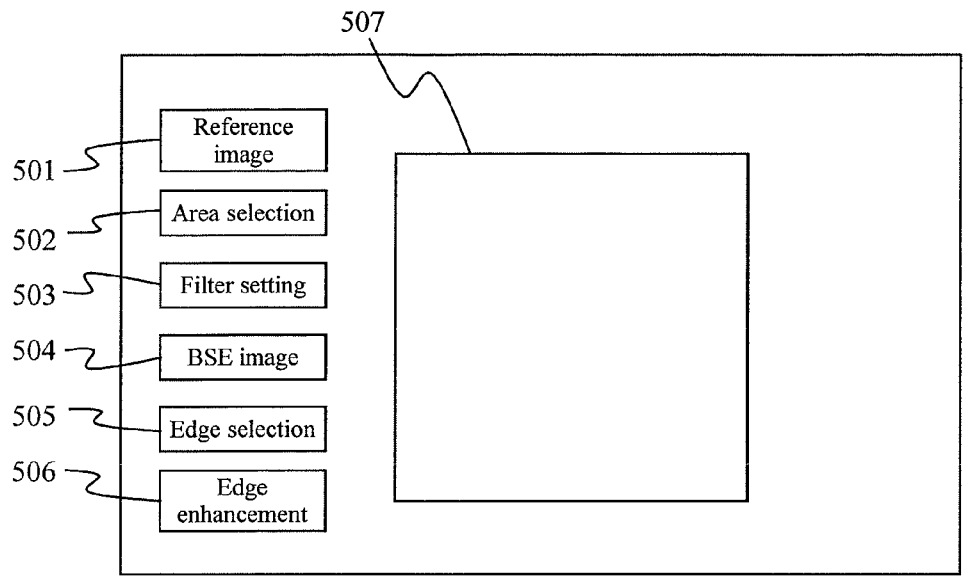
FIG. 6 shows a condition setting screen (initial image).

FIG. 5 shows the procedure that the central controller 209 executes in accordance with a processing program during setting of a detection condition. FIG. 6 shows an exemplary setting screen displayed on the display 208. The setting of the detection condition starts with acquisition of an initial image (i.e., reference image) of a measurement pattern. For acquisition of the initial image, the central controller 209 sets the filter voltage at 0 V and sets the synthesis ratio of detected signals at 1:1.

Figure 7:
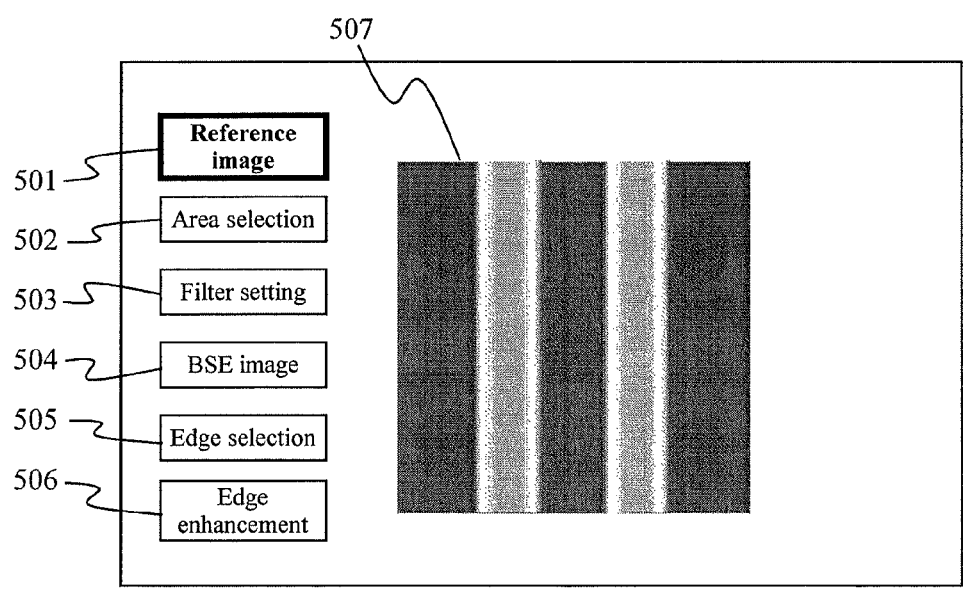
FIG. 7 shows a condition setting screen (observation screen of reference image).

For acquisition of the reference image (Step 401), the display 208 displays a screen shown in FIG. 7. The acquisition of the reference image starts with a click operation by an operator of a "reference image" button 501 on the setting screen. After the acquisition operation ends, an image display part 507 of the display 208 displays a newly acquired reference image (planar image).

When the reference image is acquired, then the procedure shifts to area input acceptance processing (Step 402). At this step, a screen to accept selection of an area by the operator is displayed so as to allow a pattern edge as a measurement target to be displayed in the image.

Figure 8:
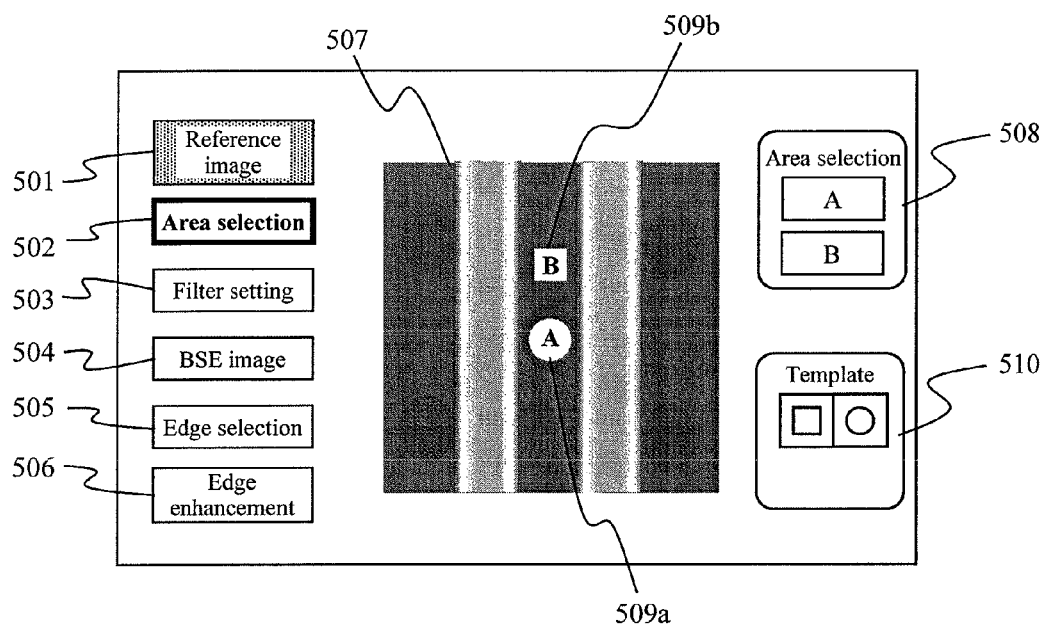
FIG. 8 shows a condition setting screen (area selection screen).

FIG. 8 shows an exemplary screen corresponding to such processing. In this screen, the operator selects two neighboring regions in the initial image. When the operator presses an "area selection" button 502 in the setting screen, then an area selection button 508 is displayed at a region by the image display part 507. On the reference image of the image display part 507, area boxes 509a and 509b are displayed in a superimposing manner. The following description calls these two area boxes an "area box A" and "area box B."

The area selection button 508 is used for selection of a type of an area box to be set on the reference image. The shape to be used to display each area box may be selected from a template 510. The operator selects a type of the area box and the shape, and disposes each area box at an appropriate position on the image. Note here that the template may be selected after disposing an area box, and the shape of the area box may be changed. The size of the area box may be changed freely between predetermined minimum and maximum values of the area of the box.

Figure 9:
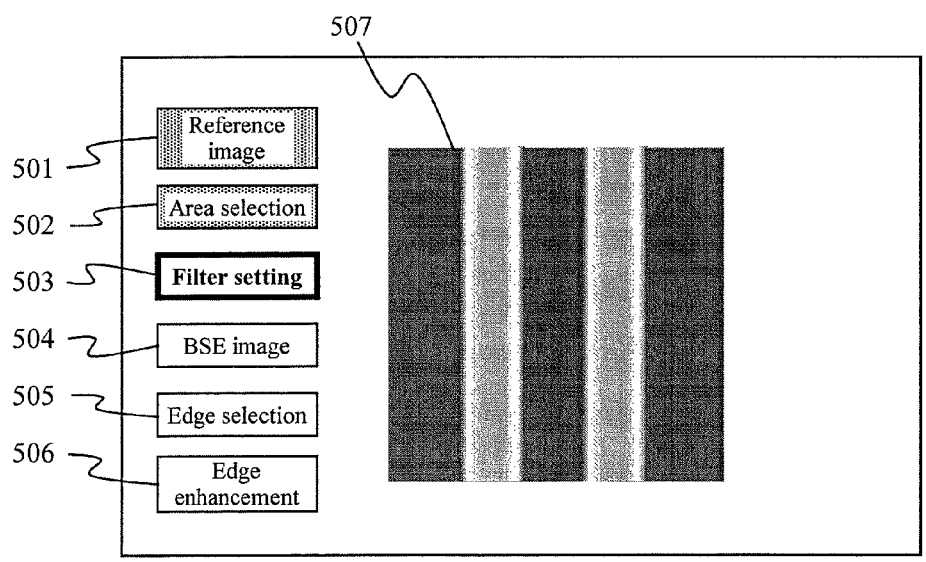
FIG. 9 shows a condition setting screen (filter setting screen).

When the selection of the area ends, the central controller 209 displays a setting screen of the filter voltage on the display 208 (Step 403). FIG. 9 shows the setting screen of the filter voltage. When the operator presses a "filter setting" button 503 on the setting screen, the central controller 209 starts processing to determine an optimum value of the filter voltage. Herein, if an image necessary for a synthesis ratio of the detected signals described later has been acquired, this setting processing of the filter voltage may be skipped.

For automatic setting processing of the filter voltage, a detected signal detected at the detector 110a only is used. Herein, the central controller 209 changes the filter voltage from the initial value step by step by a predetermined amount, and every time the filter voltage is changed, the central controller 209 acquires an image of the sample 106. Letting that the gray levels of the regions surrounded by the area boxes A and B in the image are $S_A$ and $S_B$, respectively, then every time the filter voltage is changed and a corresponding image is acquired, the central controller 209 calculates the gray level ratio $S_A/S_B$. The central controller 209 uses this gray level ratio as an evaluation value, and optimizes the filter voltage as in the following procedure.

Figures 1, 10:
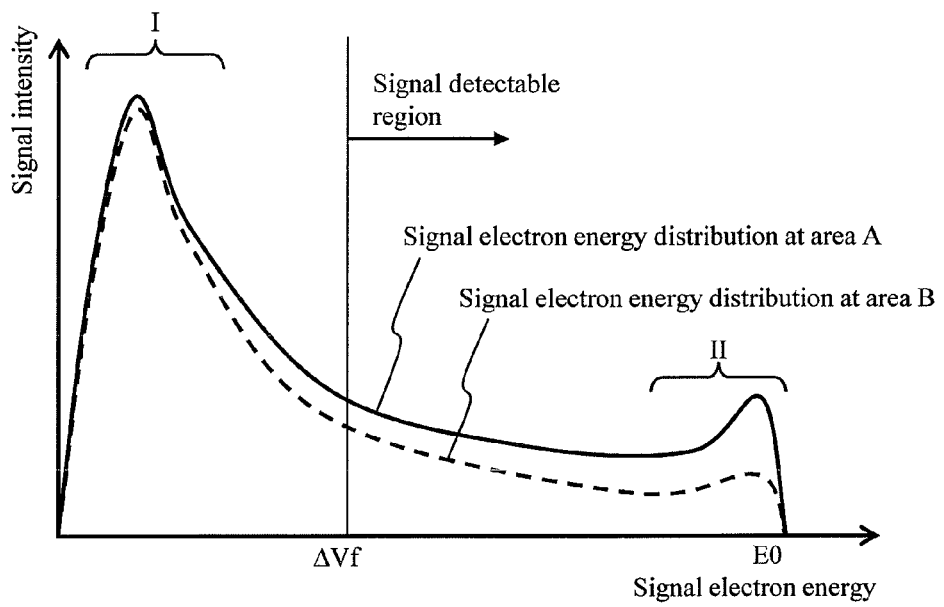
Figures 2, 10:
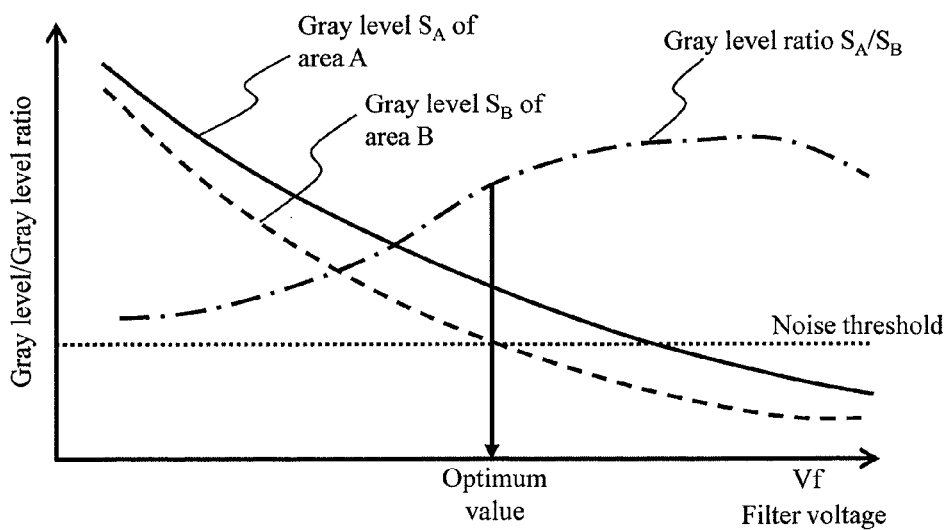
Figures 3, 10:
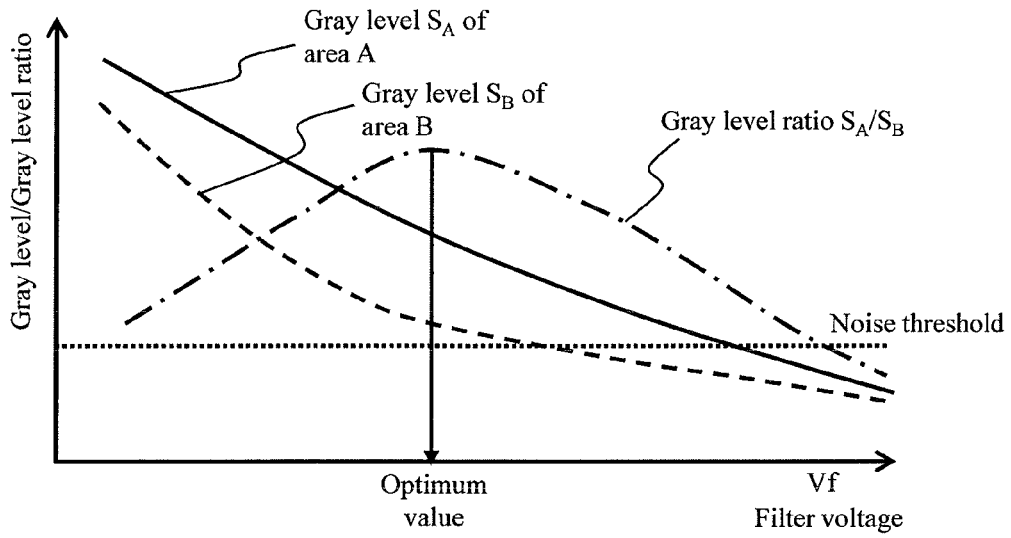
Figures 4, 10:
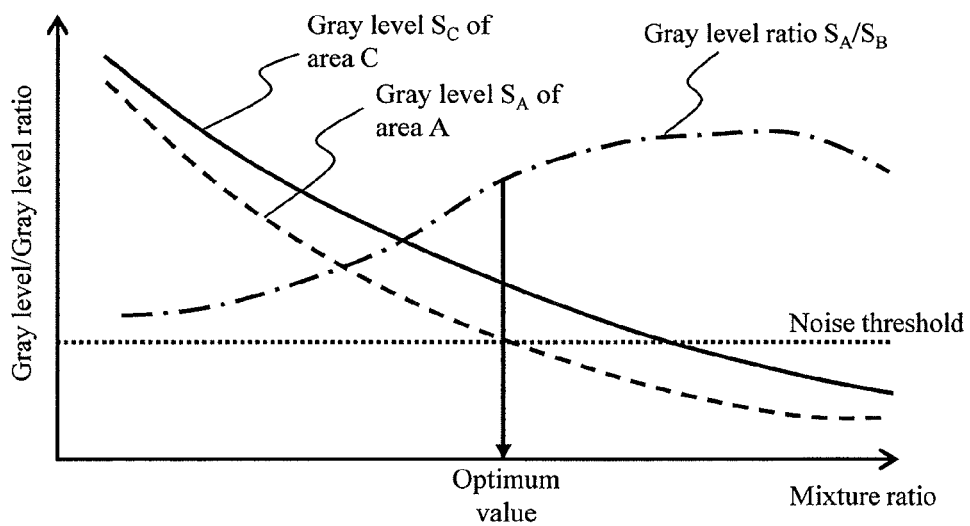
Figures 5, 10:
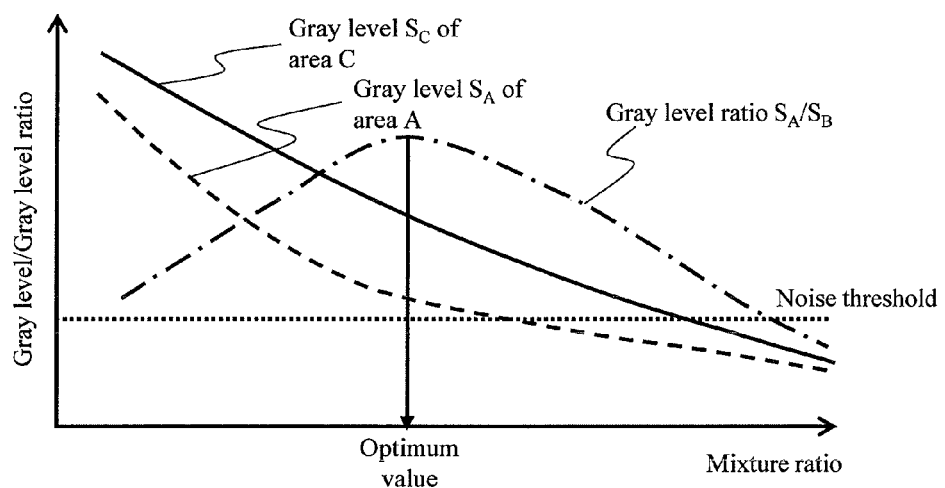

Referring now to FIGS. 10-1 to 10-3, a method to set an optimum value of the filter value is described below. FIG. 10-1 shows a relationship between energy of signal electrons and signal intensity. The horizontal axis shows the energy of signal electrons and the vertical axis represents the signal intensity. Herein, the metal part (place selected by the area box A) at the lower layer of the three-dimensional device is often made of heavy metal, and its surrounding part (place selected by the area box B) is often made of light metal.

In such a case, at a part of the detected signals for secondary electrons having low energy, a difference in intensity between them is small (region [I] in the drawing). On the other hand, at a part of the detected signals for backscattered electrons having energy close to the incident energy E0, the detection is more at the part of the area box A than at the part of the area box B (region [II] in the drawing).

As described above, the central controller 209 activates the energy filter 109 and sets finite filter voltage (in the drawing, ΔVf). Then, a signal having energy lower than ΔVf is reflected from the energy filter 109, and a signal having energy higher than ΔVf only is detected.

This means that ΔVf that is sufficiently large enables no detected signals to be detected from region [I] in FIG. 10-1. At this time, the gray level ratio $S_A/S_B$ increases. On the other hand, in the case of a too large ΔVf, absolute signal intensity of both of signals from the area box A and from the area box B becomes small, thus failing in the distinction from noise during signal detection.

Letting that the gradation (gray level) on the image corresponding to the amplitude of noise is N and the value five times it is set as a noise threshold, ΔVf can be determined so that the gray level ratio $S_A/S_B$ is maximized while keeping the gray level of the area box A>5N and the gray level of the area box B>5N. Although the noise threshold is specified as five times or more the noise amplitude N, this constant may be variable.

Referring to FIGS. 10-2 and 10-3, the following describes a method to optimize ΔVf. FIG. 10-2 shows an exemplary case where larger ΔVf makes the gray level ratio $S_A/S_B$ also larger. In this case, too large ΔVf makes $S_B$ smaller than the noise threshold. Therefore when the gray level ratio $S_A/S_B$ changes in this way, the central controller 209 sets ΔVf making $S_B$ equal to the noise threshold as the optimum value of the filter voltage.

FIG. 10-3 shows an exemplary case where the gray level ratio $S_A/S_B$ has a local maximum value with respect to ΔVf. In the range of ΔVf where both of $S_A$ and $S_B$ do not fall below the noise threshold, $S_A/S_B$ becomes maximum. Then the central controller 209 sets ΔVf where $S_A/S_B$ becomes maximum as the optimum value of the filter voltage.

The above procedure is only to quantify the evaluation value (gray level ratio $S_A/S_B$) and determine the magnitude relationship, and so it is easy to automatize the procedure. The central controller 209 sets the thus found filter voltage as the optimum value.

Figure 11:
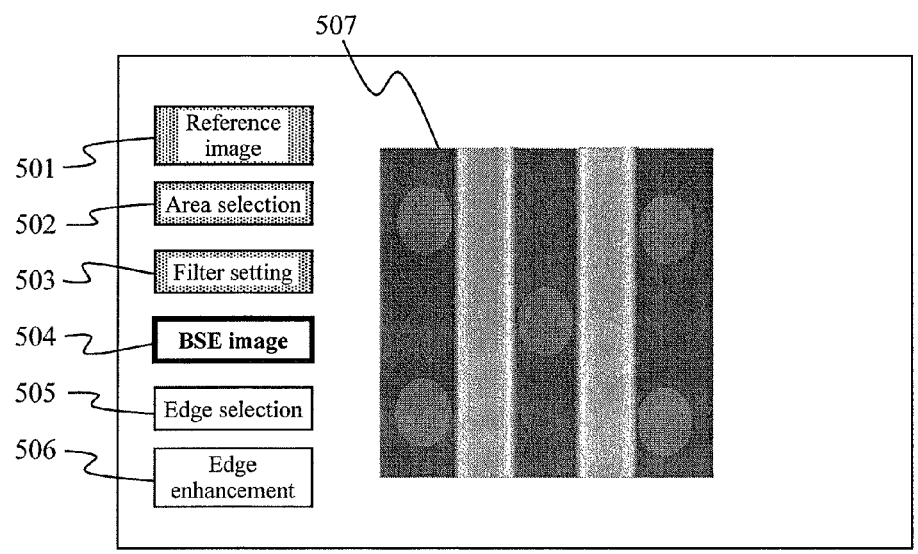
FIG. 11 shows a condition setting screen (observation screen of BSE image).

When the setting of the filter voltage ends, the central controller 209 displays an acquired image of a detected image of backscattered electrons (BSE image) (Step 404). FIG. 11 shows a setting screen of the BSE image. When the operator presses a "BSE image" button 504, the central controller 209 executes the acquisition processing of the BSE image.

In this case, the central controller 209 uses a detected signal detected at the detector 110a only. The central controller 209 acquires an image using the filter voltage optimized at Step 403. When acquiring the new image based on the optimized filter voltage, the central controller 209 displays the acquired image on the image display part 507.

Figure 12:
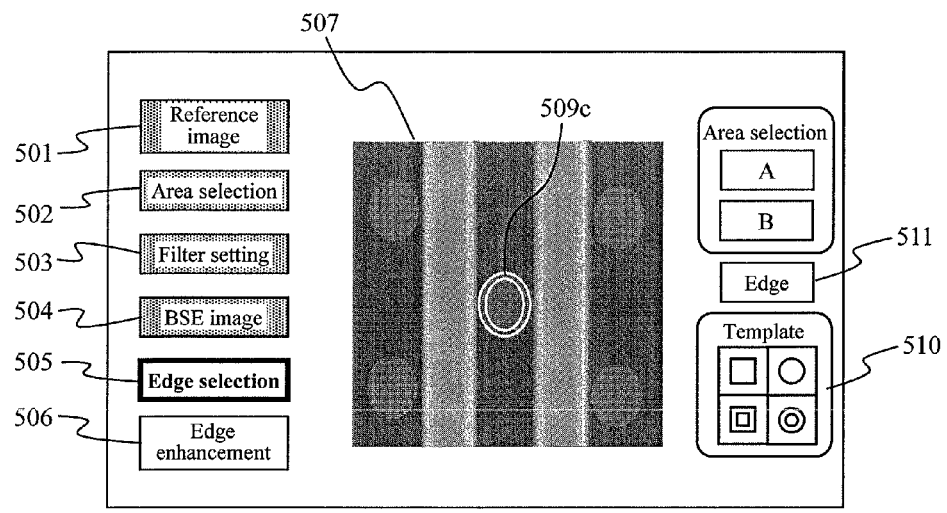
FIG. 12 shows a condition setting screen (edge selection screen).

When the BSE image is acquired, the central controller 209 executes processing to allow the operator to set and input a region of an edge to be observed in the BSE image (Step 405). FIG. 12 shows an edge selection screen. When the operator presses an "edge selection" button 505 on the setting screen, an edge selection button 511 is displayed at a region by the image display part 507. Then on the BSE image of the image display part 507, an area box 509c is displayed. This area box to designate the edge is called an "area box C" in the following description. The operator selects the shape of the area box from the template 510. Then the operator disposes the area box C at an appropriate position on the BSE image. The size of the area box C preferably is changed freely.

Figure 13:
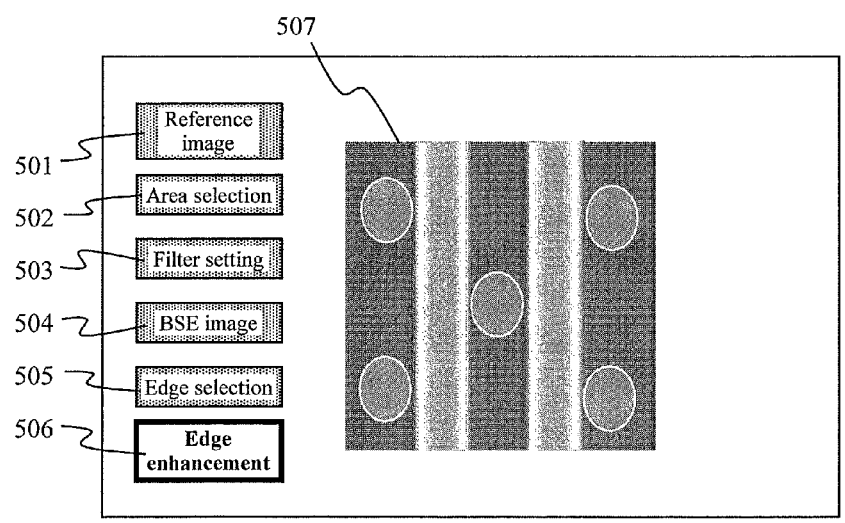
FIG. 13 shows a condition setting screen (edge enhancement screen).

When the setting of the area box C ends, the central controller 209 displays a setting screen to automatically set the mixture ratio of two detected signals on the display 208 (Step 406). FIG. 13 shows a setting screen for mixture ratio. When the operator presses an "edge enhancement" button 506 on the setting screen, the central controller 209 starts processing to automatically determine the mixture ratio of the two detectors 110a and 110b.

When starting the processing, the central controller 209 changes the mixture ratio of the detected signal of the detector 110a and the detected signal of the detector 110b step by step, and every time the mixture ratio is changed, the central controller 209 acquires a synthesized image of the two detected signals based on the set mixture ratio.

Let that the gradation (gray level) of the area box C in the image is $S_C$. Then the central controller 209 calculates the gray level ratio $S_C/S_A$. The central controller 209 uses this gray level ratio as an evaluation value, and determines an optimum mixture ratio as in the following procedure. Alternatively, the region to be compared with the area box C about the gray level may be the area box B, and the gray level ratio $S_C/S_B$ may be calculated as the evaluation value.

Referring to FIGS. 10-4 and 10-5, the following describes a method to optimize the mixture ratio. FIG. 10-4 shows an exemplary case where a larger mixture ratio makes the gray level ratio $S_C/S_A$ also larger. A too large mixture ratio makes $S_A$ smaller than the noise threshold. Therefore when the gray level ratio $S_C/S_A$ changes in this way, the central controller 209 sets the mixture ratio making $S_A$ equal to the noise threshold as the optimum value.

On the other hand, FIG. 10-5 shows an exemplary case where the gray level ratio $S_C/S_A$ has a local maximum value with respect to the mixture ratio. In the range of the mixture ratio where both of $S_C$ and $S_A$ do not fall below the noise threshold, $S_C/S_A$ becomes maximum. Then, the central controller 209 sets the mixture ratio where $S_C/S_A$ becomes maximum as the optimum value.

Summary

With the above procedure, the central controller 209 automatically optimizes the mixture ratio of the filter voltage and the detected signals, and acquires an image under the condition where the gray level ratio becomes the best. This enables automatic setting of the optimum mixture ratio of true secondary electrons and backscattered electrons for the sample 106 as the measurement target. This enables observation of the opening 303 that is the second darkest in the image and has a small difference in gradation (gray levels) from the darkest region. Then, even for a three-dimensional device having an unknown structure, the dimensions of the opening 303 can be measured under the optimum condition.

In the above embodiment, the filter voltage is set at 0 V and the synthesis ratio of detected signals is set at 1:1 during the acquisition of the reference image, and these values may be freely set by an operator.

In the above embodiment, when determining the filter voltage at Step 403, an image during the processing is not displayed. The list of each image when the filter voltage is changed step by step may be displayed. Then the operator who checks the list of these images may set the condition of any selected image as the filter setting voltage.

In the above embodiment, when determining the synthesis ratio of two detected signals at Step 406, an image during the processing is not displayed. Alternatively, the list of each image when the synthesis ratio is changed step by step may be displayed. Then the operator who checks the list of these images may set the condition of any selected image as the synthesis ratio.

Embodiment 2

FIGS. 14(a) to (c) show another exemplary surface pattern of a three-dimensional device that is assumed as a measurement target. This assumed three-dimensional device is a lattice-shaped device where a horizontally extending line and space pattern 601 (hereinafter called "lower layer line 601") and a vertically extending line and space pattern 602 (hereinafter called "upper layer line 602") are laminated.

The area of a gap part 603 other than a region where the upper layer line 602 and the lower layer line 601 cross each other determines the device characteristics, and so the dimension control is required thereto. Therefore the horizontal width of the gap part 603 has to be measured, and the edge of the lower layer line 601 and the edge of the upper layer line 602 have to be clarified while emphasizing the contrast between the lower layer line 601 and the gap part 603.

Figure 15:
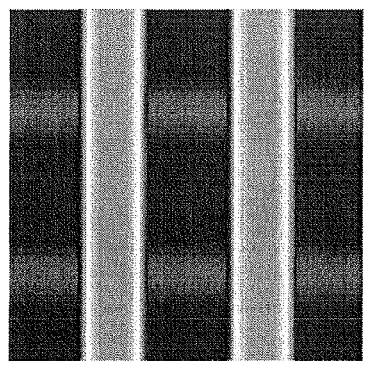
FIG. 15 shows an exemplary image when condition setting is executed.
Figure 15:
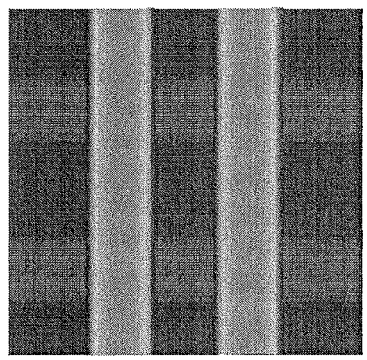
Figure 15:
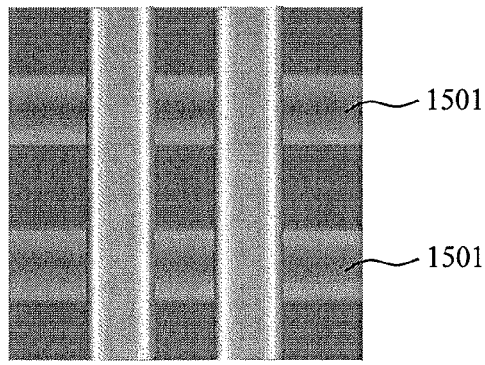

When the height of the lines of the upper layer line 601 is larger than the width between lines, the space between lines is like a deep groove, thus making it difficult to determine the presence or not of the lower layer line 601. The method shown in FIG. 5 enables the optimization of the setting parameters in this device also. FIGS. 15(a) to (c) show an exemplary image when Step 401 to Step 406 are executed. As is understood from the comparison between FIGS. 15(a) and (c), FIG. 15(c) subjected to adjustment of the mixture ratio includes a horizontal stripe pattern 1501 that is not displayed in FIG. 15(a).

Embodiment 3

Figure 14:
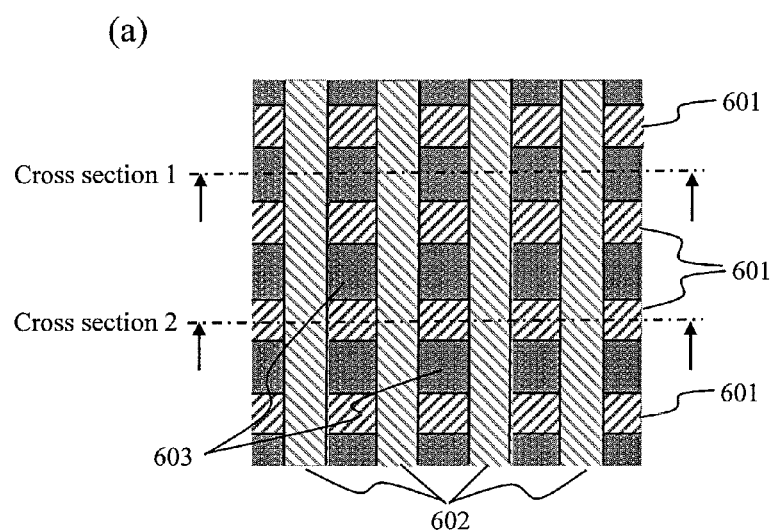
FIG. 14 shows an exemplary structure of a pattern that is a measurement target in Embodiment 2.
Figure 14:
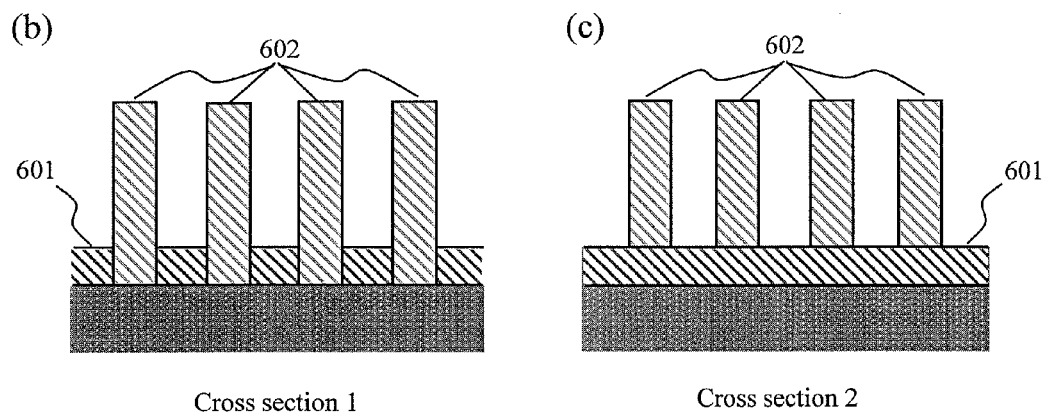
Figure 16:
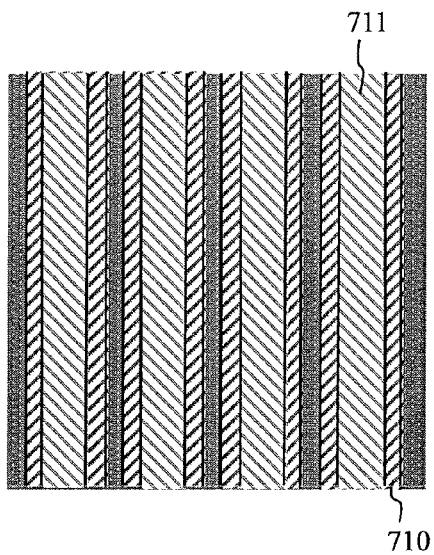
FIG. 16 shows an exemplary structure of a pattern that is a measurement target in Embodiment 3.
Figure 16:
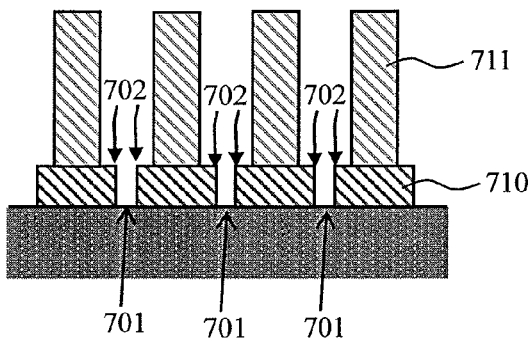
Figure 16:
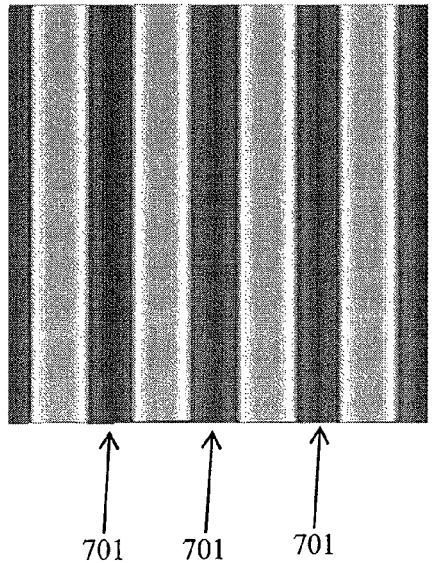

The three-dimensional device that is measurable as a measurement target is not limited to the three-dimensional devices shown in FIG. 4 and FIG. 14. The measurement is suitable to a three-dimensional device having a pattern structure shown in FIGS. 16(a) to (c) as well. The assumed three-dimensional device shown in these drawings has a shape as shown in FIG. 15(b) such that a base layer 710 is separated in the direction where a pattern 711 is aligned. As shown in FIG. 15(b), this pattern structure includes three layers having different height positions viewed from the irradiation direction of the primary electron beam. This means that the structure including three typical levels of brightness is assumed for detected signals.

Herein, the step height between the base layer 710 and its substrate is small. Therefore, a difference in brightness is small. Then when there is a need at Step 401 for the acquisition of a reference image to emphasize the shape of a darkest part 701 and emphasize an outline 702 of the border between the darkest part and the adjacent part, the aforementioned method of the present invention is applicable.

Actually Step 403 corresponds to a step to emphasize the shape of the darkest part 701 and Step 406 corresponds to a step to emphasize the outline 702.

Exemplary Configuration 2

Figure 17:
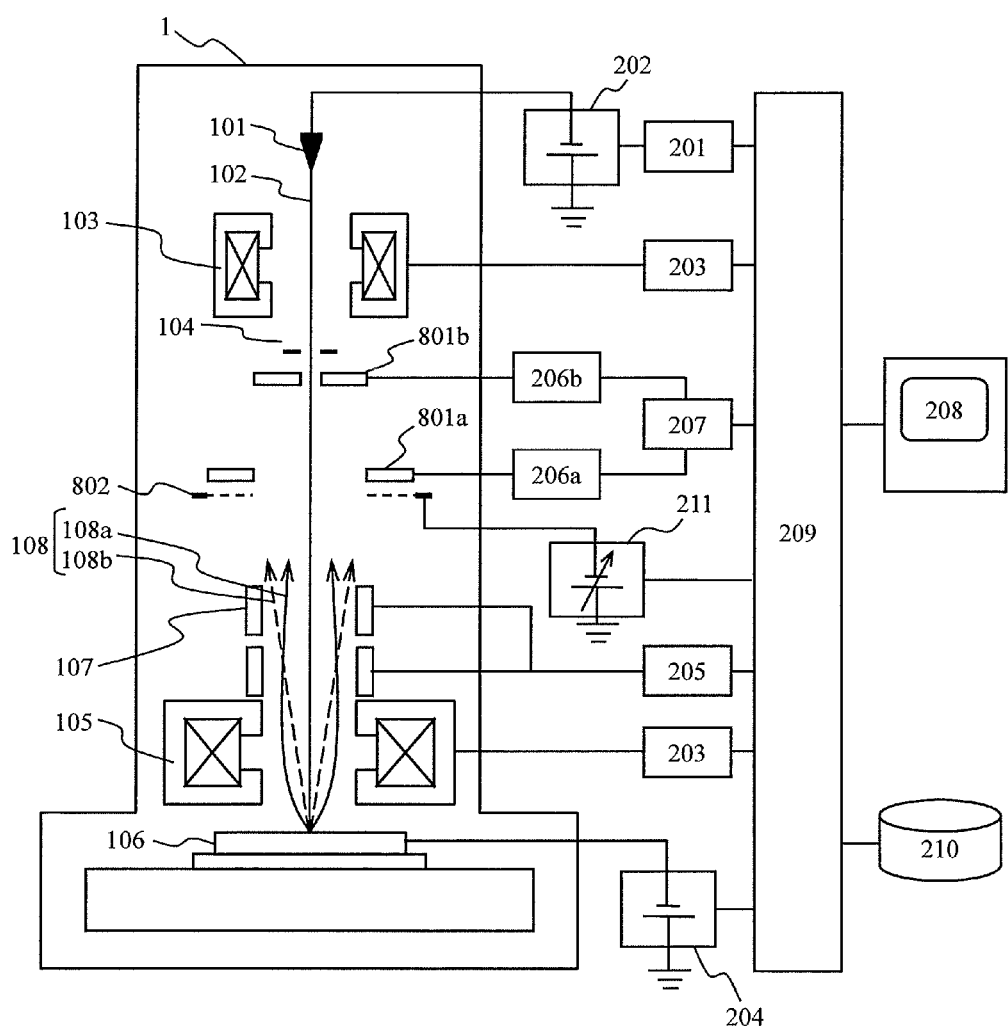
FIG. 17 shows a second exemplary configuration of a scanning electron microscope.

FIG. 17 shows an exemplary structure of a scanning electron microscope according to another exemplary configuration. FIG. 17 shows elements corresponding to those of FIG. 1 with the same reference numerals. In this exemplary configuration, an annular detector 801a having a large opening with respect to the central axis detects signal electrons 108 extending over a wide range from the central axis like backscattered electrons (BSE) 108b. On the other hand, a disk-shaped detector 801b having an opening at the center to let a primary electron beam 102 pass therethrough detects signal electrons 108 accelerated by retarding voltage 204 and not extending over a wide range from the central axis like true secondary electrons (TSE) 108a.

Signals detected at the detector 801a and the detector 801b are amplified by amplifiers 206a and 206b, respectively, and then these signals undergo image operation at the synthesis operation part 207 and are displayed on the display 208.

The detectors 801a and 801b are disposed at different heights in the central axis direction. Below the detected face of the detector 801a, an annular filter mesh 802 having a shape similar to that of the detector is disposed. To the filter mesh 802, a filter power source 211 is connected, and filter voltage is controlled by a central controller 209.

In this way, when the scanning electron microscope includes a detector to detect signal electrons that have passed through the energy filter and a detector to detect signal electrons that do not pass through nor collide with the energy filter, the technique described in the exemplary configuration 1 is directly applicable to such a scanning electron microscope as well.

Exemplary Configuration 3

Figure 18:
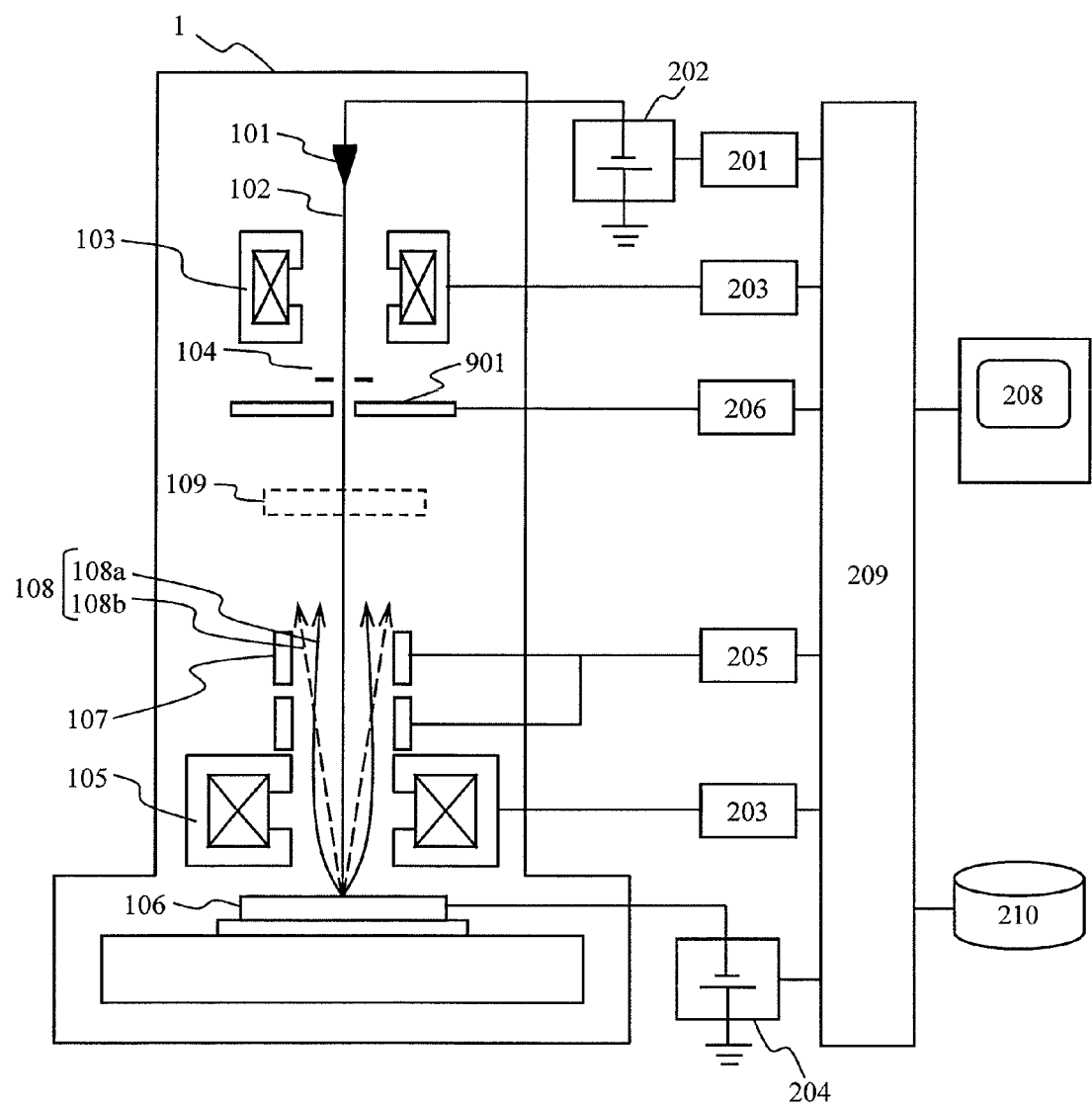
FIG. 18 shows a third exemplary configuration of a scanning electron microscope.

FIG. 18 shows still another exemplary configuration of a scanning electron microscope. Similarly to the exemplary configuration 1, the scanning electron microscope according to this exemplary configuration includes an energy filter 109 that separates signal electrons 108 generated from the sample 106 according to their energy levels.

In the present exemplary configuration, however, the scanning electron microscope includes a detector 901 only that detects secondary electrons that have passed through the energy filter 109. In this case, signals detected at the detector 901 are amplified by an amplifier 206 and are displayed on a display 208.

In the present exemplary configuration, the energy filter 109 is configured as in FIG. 2. When the detector 901 is configured like a disk-shape having an opening letting a primary electron beam 102 pass therethrough, the optimum value of the filter power source 211 to acquire a backscattered electrons (BSE) image due to a difference in material contrast can be determined easily by executing Steps 401 to 403 shown in FIG. 5.

Exemplary Configuration 4

Figure 19:
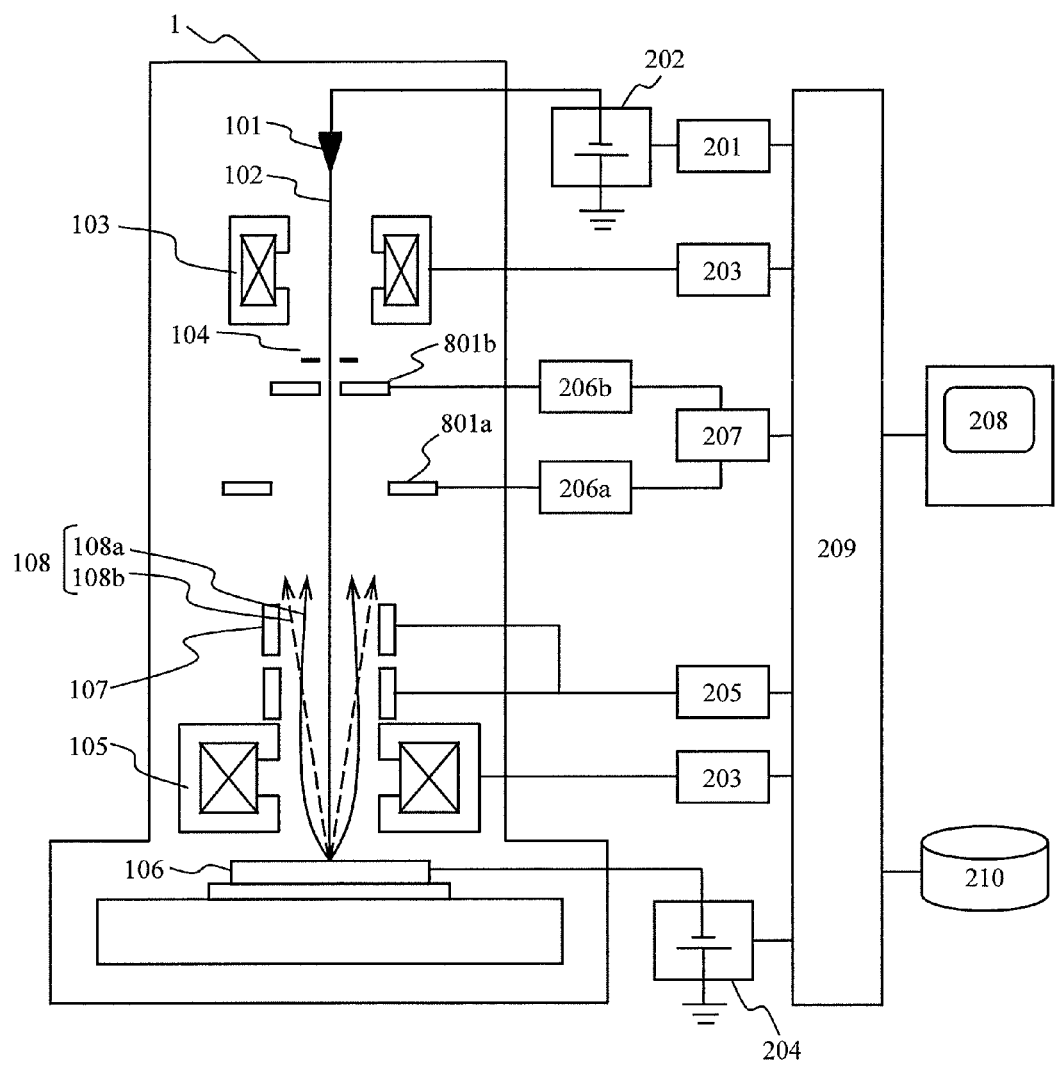
FIG. 19 shows a fourth exemplary configuration of a scanning electron microscope.

When two detectors can detect separately two types of signal electrons that are different in emission angle and energy level, the scanning electron microscope may not have an energy filter as in FIG. 19 showing elements corresponding to those in FIG. 1 with the same reference numerals. In this case, there is no need to adjust an energy filter. In this case also, the mixture ratio of two detected signals can be automatically determined by executing Steps 404 to 406 shown in FIG. 5.

Exemplary Configuration 5

All of the aforementioned exemplary configurations describe the configuration of applying the retarding voltage 204. However, the retarding voltage 204 may not be applied. Alternatively, in another configuration, the retarding voltage 204 is not applied, an electrode to apply positive voltage is disposed immediately above the sample, and signal electrons 108 output from the sample 106 is drawn upward at an accelerated rate. Needless to say, in still another configuration, the retarding voltage 204 may be applied, the signal electrons 108 may be drawn upward, and an electrode to apply positive voltage for acceleration may be disposed.

Other Exemplary Configurations

The present invention is not limited to the above-described embodiments, and may include various modification examples. For instance, the entire detailed configuration of the embodiments described above for explanatory convenience is not always necessary for the present invention. A part of one embodiment may be replaced with the configuration of another embodiment, or the configuration of one embodiment may be added to the configuration of another embodiment. The configuration of each embodiment may additionally include another configuration, or a part of the configuration may be deleted or replaced.

The above-described configurations, functions, processing parts, processing means and the like, a part or the entire of them, may be implemented by an integrated circuit or other types of hardware, for example. Alternatively, the above-described configurations, functions and the like may be implemented by software using a processor that interprets a program to implement these functions and executes the program. Information such as programs, tables and files to implement these functions may be placed on a recording device such as a memory, a hard disk or a SSD (Solid State Drive), or a recording medium such as an IC card, a SD card or a DVD.

Control lines and information lines illustrated are those considered necessary for the description, and all of the control lines and information lines necessary for the product are not always shown. It can be considered that almost all configurations are mutually connected actually.

REFERENCE SIGNS LIST

1 Electron microscope lens barrel
101 Electron emitting source
102 Primary electron beam
103 Focusing lens
104 Current limiting aperture
105 Objective lens
106 Sample
107 Deflector
108 Signal electrons
108a True secondary electrons
108b Backscattered electrons
109 Energy filter
110a Detector
110b Detector
120 Converting electrode
130, 131 Secondary electrons
201 Controller
203a, 203b Controller
205 Controller
204 Retarding voltage
206a, 206b Amplifier
207 Synthesis operation part
208 Display

The invention claimed is:
1. A charged particle beam apparatus, comprising:
a charged particle source configured to irradiate a sample with a primary charged particle beam;
a first detector configured to detect a first signal electron having first energy from signal charged particles generated from the sample;
a second detector configured to detect a second signal electron having second energy from signal charged particles generated from the sample;
a first operation part configured to change a synthesis ratio of a signal intensity of the first signal electron and a signal intensity of the second signal electron and to generate a detected image corresponding to each synthesis ratio;
a second operation part configured to calculate a ratio of signal intensities corresponding to predetermined two areas of the detected image generated for each synthesis ratio; and
a third operation part configured to determine a mixture ratio to be used for acquisition of the detected image on a basis of a change of the ratio of signal intensities.
2. The charged particle beam apparatus according to claim 1, wherein
the third operation part determines, in a range where both of two signal intensities corresponding to the two areas are larger than a predetermined threshold, a synthesis ratio giving a maximum value of the ratio of signal intensities as a mixture ratio to be used to acquire the detected image.
3. The charged particle beam apparatus according to claim 1, wherein
one of the two areas is an area designating an edge designated by an operator on a display screen.
4. The charged particle beam apparatus according to claim 1, further comprising an energy filter that separates signal charged particles to be detected by the first detector and the second detector according to magnitude of energy.

5. The charged particle beam apparatus according to claim 4, further comprising:
a fourth operation part configured to change filter voltage to be applied to the energy filter and to generate a detected image corresponding to each filter voltage;
a fifth operation part configured to calculate a ratio of signal intensities corresponding to predetermined two areas of the detected image generated for each filter voltage; and
a sixth operation part configured to determine filter voltage to be used for acquisition of the detected image on a basis of a change of the ratio of signal intensities.
6. The charged particle beam apparatus according to claim 5, wherein
the sixth operation part determines, in a range where both of two signal intensities corresponding to the two areas are larger than a predetermined threshold, filter voltage giving a maximum value of the ratio of signal intensities as filter voltage to be used to acquire the detected image.
7. The charged particle beam apparatus according to claim 5, wherein
the two areas are areas designated by an operator on a display screen.
8. The charged particle beam apparatus according to claim 4, wherein
the first detector detects, of the signal charged particles, secondary electrons generated from signal charged particles that have passed through the energy filter, and
the second detector detects, of the signal charged particles, secondary electrons generated from collision with the energy filter.
9. The charged particle beam apparatus according to claim 4, wherein
the first detector detects, of the signal charged particles, signal charged particles that do not pass through the energy filter, and
the second detector detects, of the signal charged particles, signal charged particles that have passed through the energy filter.
10. A charged particle beam apparatus, comprising:
a charged particle source configured to irradiate a sample with a primary charged particle ray;
an energy filter configured to separate signal charged particles according to magnitude of energy;
a detector configured to detect signal charged particles that have passed through the energy filter;
a first operation part configured to change filter voltage to be applied to the energy filter and to generate a detected image corresponding to each filter voltage;
a second operation part configured to calculate a ratio of signal intensities corresponding to predetermined two areas of the detected image generated for each filter voltage; and
a third operation part configured to determine filter voltage to be used for acquisition of the detected image on a basis of a change of the ratio of signal intensities.
11. The charged particle beam apparatus according to claim 10, wherein
the third operation part determines, in a range where both of two signal intensities corresponding to the two areas are larger than a predetermined threshold, filter voltage giving a maximum value of the ratio of signal intensities as filter voltage to be used to acquire the detected image.
12. The charged particle beam apparatus according to claim 10, wherein
the two areas are areas designated by an operator on a display screen.

13. A pattern measurement method in a charged particle beam apparatus comprising: a charged particle source configured to irradiate a sample with a primary charged particle ray; a first detector configured to detect a first signal electron having first energy from signal charged particles generated from the sample; and a second detector configured to detect a second signal electron having second energy from signal charged particles generated from the sample, the method comprising the following steps of:
- a first step of changing a synthesis ratio of a signal intensity of the first signal electron and a signal intensity of the second signal electron and generating a detected image corresponding to each synthesis ratio;
- a second step of calculating a ratio of signal intensities corresponding to predetermined two areas of the detected image generated for each synthesis ratio;
- a third step of determining a mixture ratio to be used for acquisition of the detected image on a basis of a change of the ratio of signal intensities; and
- a fourth step of measuring a pattern on a basis of a detected image acquired using the determined mixture ratio.

14. A pattern measurement method in a charged particle beam apparatus comprising: a charged particle source configured to irradiate a sample with a primary charged particle ray; an energy filter configured to separate signal charged particles according to magnitude of energy; and a detector configured to detect signal charged particles that have passed through the energy filter; the method comprising the following steps of:
- a first step of changing filter voltage to be applied to the energy filter and generating a detected image corresponding to each filter voltage;
- a second step of calculating a ratio of signal intensities corresponding to predetermined two areas of the detected image generated for each filter voltage;
- a third step of determining filter voltage to be used for acquisition of the detected image on a basis of a change of the ratio of signal intensities; and
- a fourth step of measuring a pattern on a basis of a detected image acquired using the determined filter voltage.

* * * * *